(12) United States Patent
Fujii et al.

(10) Patent No.: US 9,119,535 B2
(45) Date of Patent: Sep. 1, 2015

(54) BLOOD PRESSURE MANOMETER AND A METHOD OF CALCULATING INDICES OF ATHEROSCLEROSIS USING THE BLOOD PRESSURE MANOMETER

(75) Inventors: Kenji Fujii, Kyoto (JP); Tatsuya Kobayashi, Otsu (JP); Toshihiko Ogura, Inuyama (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 855 days.

(21) Appl. No.: 13/314,355

(22) Filed: Dec. 8, 2011

(65) Prior Publication Data

US 2012/0172734 A1    Jul. 5, 2012

(30) Foreign Application Priority Data

Dec. 8, 2010   (JP) ................................. 2010-273487

(51) Int. Cl.
*A61B 5/02* (2006.01)
*A61B 5/021* (2006.01)
*A61B 5/0225* (2006.01)

(52) U.S. Cl.
CPC ........... *A61B 5/02007* (2013.01); *A61B 5/0225* (2013.01); *A61B 5/02125* (2013.01)

(58) Field of Classification Search
CPC ............................................... A61B 5/022086
USPC ........................................................ 600/493
See application file for complete search history.

(56) References Cited

U.S. PATENT DOCUMENTS

| 2,565,011 | A | 11/1993 | O'Rourke |
| 6,616,613 | B1 * | 9/2003 | Goodman ..................... 600/504 |
| 2004/0167414 | A1 * | 8/2004 | Tanabe et al. ................ 600/500 |

OTHER PUBLICATIONS

Westerhoff et al: "Quantification of Wave Reflection in the Human Aorta From Pressure Alone: A Proof of Principle" Hypertension, 2006, pp. 48; 595-601.
London et al: "Increased Systolic Pressure in Chronic Uremia. Role of Arterial Wave Refections" Hypertension, 1992, pp. 20: 10-19.

* cited by examiner

*Primary Examiner* — Patricia Mallari
*Assistant Examiner* — Vasuda Ramachandran
(74) *Attorney, Agent, or Firm* — Osha Liang LLP

(57) ABSTRACT

A blood pressure measurement device accurately calculates an index useful in determining the degree of arteriosclerosis by accurately detecting a difference in time of appearance of a ejection wave and reflected wave in a blood pressure waveform. The device sets a threshold value based on an index that expresses a characteristic of the blood pressure waveform with respect to the point of appearance of the reflected wave in the blood pressure and estimates a rise point of the reflected wave by calculating an x-coordinate value of a point based on a maximum amplitude of the reflected wave and the threshold value. The device obtains the index of degree of arteriosclerosis by calculating a time difference in appearance between the ejection wave and the reflected wave based on the estimated rise point of the reflected wave.

6 Claims, 14 Drawing Sheets

(A)

(B)

(A)

(B)

(A)

(B)

(A)

(B)

Amplitude of reflected wave magnified (A)

Maximum amplitude of reflected wave (1) × Threshold value (20%) = 0.2*

(B)

BLOOD PRESSURE MANOMETER AND A METHOD OF CALCULATING INDICES OF ATHEROSCLEROSIS USING THE BLOOD PRESSURE MANOMETER

BACKGROUND OF INVENTION

The present invention relates to a blood pressure measurement device and a method of calculating an index of the degree of arteriosclerosis using the device, and in particular to a blood pressure measurement device measuring blood pressure data useful in determining an index of arteriosclerosis, and a method of calculating an index of the degree of arteriosclerosis using said device.

Previously, devices determined the degree of arteriosclerosis by finding the speed of propagation of pulse waves emitted from the heart (PWV: pulse wave velocity). Because the speed of pulse wave propagation becomes faster as arteriosclerosis advances, the PWV is a useful indicator for determining the degree of arteriosclerosis and has continued to be generally used in medical facilities etc. as the standard indicator for determining the degree of arteriosclerosis up to the present time. PWV measurement devices measure pulse waves by affixing a cuff etc. to at least two locations such as the upper arm or lower extremities etc., and thereby are able to calculate the difference in time between appearance of each pulse wave (ejection wave, reflected wave) from the length etc. of arteries at the two points where the cuffs etc. are attached to measure the pulse wave. This time difference is used as the Tr (Traveling time to reflected wave) and is another indicator of the degree of arteriosclerosis.

However, the equipment required to perform the aforementioned PWV measurement is expensive. Furthermore, because of the requirement to attach the cuffs to at least two locations such as the upper arm or lower extremities etc. in order to measure the pulse wave, it is difficult to measure pulse wave propagation velocity PWV easily at home. Accordingly, technologies have been proposed whereby the degree of arteriosclerosis is determined only from the pulse wave at the upper arm or carotid artery.

Technology for determining the degree of arteriosclerosis from the pulse wave in the upper arm only, such as in Patent Laid-open 2004-113593 ("Patent Reference 1") (the disclosure of which is incorporated herein by reference), discloses an evaluation device providing a cuff for measuring the pulse wave and a pressure cuff compressing the peripheral end. Using this device, it is possible to compress the peripheral end while measuring the pulse wave at the heart end. By this means, the ejection wave ejected from the heart can be separated from the reflected wave from the iliac artery branch and various parts of the artery. Thus, it is possible to determine the degree of arteriosclerosis by calculation of the time difference and ratio of strength of the peaks of the advancing wave component and reflected wave component(s).

In order to accurately determine the degree of arteriosclerosis by means of the technology disclosed in Patent Reference 1, it is necessary to accurately detect the point of origin of a reflected wave from the pulse wave. A method for this purpose, such as in Patent Publication 2009-517140 (the disclosure of which is incorporated herein by reference), is disclosed as a method of separating the ejection wave and reflected wave using the estimated values of the blood pressure waveform and blood flow volume waveform of the aorta. FIG. 16(A) and FIG. 16(B) are drawings for the purpose of explaining the method of Patent Reference 2, wherein a ejection wave (the advancing wave in the drawing) and reflected wave are separated from a blood pressure wave, which is a composite wave of an ejection wave and reflected wave as shown in FIG. 16(A).

In the method according to Patent Reference 2, a blood pressure waveform estimated by the transfer function method, from the blood pressure wave measured at a peripheral artery in the upper body (such as the radial artery or brachial artery etc.), or a blood pressure waveform measured from the carotid artery, is used to approximate the value of the blood pressure wave of the artery. The aforementioned transfer function method is disclosed in U.S. Pat. No. 5,265,011. As for the blood flow volume wave, as stated in Non-patent Reference 1 (B. E. Westerhof et al., Quantification of wave reflection in the human aorta from pressure alone: a proof of principle. *Hypertension* 2006; 48; 595-601) (the disclosure of which is incorporated herein by reference), a triangular waveform is used, taking from the rise of the blood pressure waveform to the incisural notch as the base, and the peak or heart contraction as the apex. In the method according to Patent Reference 2, the ejection wave and reflected wave are thus separated, and the mutual relationship thereof is calculated, and the time of highest correlation is detected as the time difference between appearance of the ejection wave and reflected wave.

However, in the aforementioned mutual relation method, it is possible to detect the time difference between the appearance of the two waveforms with good accuracy from mutual correlation if the two waveforms are respectively similar to each other. However, if the shapes of the waveforms are different, the margin of error in detection of the time difference between the appearance is increased. The blood pressure wave changes in form after the ejection wave from the heart propagates through the aorta. Also, the manner of this change in form varies according to the degree of arteriosclerosis etc. and the state of the patient. Thus, there are instances in which the time difference between the appearance of the ejection wave and the appearance of the reflected wave cannot be detected accurately from mutual correlation.

FIG. 17 shows the relationship between Tr calculated from pulse wave propagation time between two points, measured by a PWV measurement device according to prior art ("PWV Tr"), and Tr derived using prior art from actual measurement of the blood pressure wave in the carotid artery in approximately 200 individuals. The PWV Tr value calculated from pulse wave propagation velocity measured between the two points of the heart and femoral aorta using a PWV measurement device and the propagation distance of said two points is considered the most accurate Tr value that can be measured using a non-invasive measurement device at the present time. In comparison, the aforementioned Tr value derived from the blood pressure waveform in the carotid artery is obtained by detection of a time difference, between a ejection wave and a reflected wave separated using a blood flow waveform in the shape of a triangular wave and a blood pressure waveform, by means of the aforementioned mutual correlation method. From the results in FIG. 17, it is clear that in many subjects, the value of Tr derived from the aforementioned blood pressure wave in the carotid artery is calculated to be longer than the Tr value obtained using a PWV measurement device. This result is considered to indicate that a clear margin of error is present in a time difference between the appearance of the ejection wave and the reflected wave detected by means of a mutual correlation method from the pulse waveform in the carotid artery.

Also, as a method of determining the rise point of the pulse wave (reflected wave), a method is known whereby a given percentage of the pulse wave amplitude (for example 10% or 20%) is set as a threshold value, and the point where said threshold value is reached is estimated to be the rise point of the reflected wave. FIGS. 18(A) and (B) describe a method of estimating the rise point of the reflected wave using a threshold value. The ejection wave and reflected wave (FIG. 18(A)) from measured blood pressure waveforms in measured subjects are separated using the method of mutual correlation, and then the maximum amplitude of the reflected wave is enlarged until it is the same as the maximum amplitude of the ejection wave (FIG. 18(B)). Assuming that the threshold value is set at 20%, the X-axis coordinate of the point at which the amplitude of the reflected wave reaches the maximum amplitude of the reflected wave ("1" in FIG. 18(B)) multiplied by the 20% threshold value ("0.2*") is estimated to be the rise point of the reflected wave. Tr is calculated by estimating the time difference between the rise point of the ejection wave and the rise point of the reflected wave (FIG. 18(B)). However, as described above, in cases where the shapes of the blood pressure waveforms are not similar to each other and are large, then even the use of the threshold value ratio as described above will not in some cases accurately detect the time difference between the appearance of the ejection wave and the reflected wave.

Accordingly, one or more embodiments of the present invention provide a blood pressure data measurement device capable of accurately calculating a useful index for determining the degree of arteriosclerosis by accurately detecting the time difference in the appearance of the ejection wave and the reflected wave from the blood pressure waveform, and a method of calculating an index for the degree of arteriosclerosis by means of said device.

SUMMARY OF INVENTION

According to one or more embodiments of the present invention, a device for measuring blood pressure and calculating an index of degree of arteriosclerosis of a patient includes a cuff for wrapping around a measurement location of a patient, the cuff containing an air bladder; an air pressure adjustor for adjusting an internal pressure of the air bladder; a pressure sensor for detecting changes of the internal pressure of the air bladder; and a computation device for obtaining a blood pressure waveform based on the changes of internal pressure of the air bladder detected by the pressure sensor, separating and identifying an ejection wave component and a reflected wave component from the blood pressure waveform, and calculating an index of degree of arteriosclerosis of the patient. The computation device further includes: a threshold value setting portion for setting a threshold value based on an index that expresses a characteristic of blood pressure waveform with respect to the point of appearance of the reflected wave in the blood pressure waveform, and a rise point estimating portion for estimating a rise point of the reflected wave by calculating x-coordinate value of a point based on a maximum amplitude of the reflected wave and the threshold value. The index of degree of arteriosclerosis is obtained by calculating a time difference in appearance between the ejection wave and the reflected wave based on the estimated rise point of the reflected wave.

According to one or more embodiments of the present invention, a device for measuring blood pressure and calculating an index of degree of arteriosclerosis of a patient includes: means containing an air bladder for wrapping around a measurement location of a patient; means for adjusting an internal pressure of the air bladder; means for detecting changes of the internal pressure of the air bladder; and means for obtaining a blood pressure waveform based on the changes of internal pressure of the air bladder detected by the pressure sensor, separating and identifying an ejection wave component and a reflected wave component from the blood pressure waveform, and calculating an index of degree of arteriosclerosis of the patient. The means further includes: means for setting portion for setting a threshold value based on an index that expresses a characteristic of blood pressure waveform with respect to the point of appearance of the reflected wave in the blood pressure waveform, and means for estimating a rise point of the reflected wave by calculating x-coordinate value of a point based on a maximum amplitude of the reflected wave and the threshold value. The index of degree of arteriosclerosis is obtained by calculating a time difference in appearance between the ejection wave and the reflected wave based on the estimated rise point of the reflected wave.

According to one or more embodiments of the present invention, a method of calculating an index of degree of arteriosclerosis of a patient includes: obtaining a blood pressure waveform of the patient based on changes of internal pressure of an air bladder placed at a measurement location of the patient; separating and identifying an ejection wave component and a reflected wave component from the blood pressure waveform; setting a threshold value based on an index that expresses a characteristic of blood pressure waveform with respect to the point of appearance of the reflected wave in the blood pressure waveform; estimating a rise point of the reflected wave by calculating x-coordinate value of a point based on a maximum amplitude of the reflected wave and the threshold value; and obtaining the index of degree of arteriosclerosis by calculating a time difference in appearance between the ejection wave and the reflected wave based on the estimated rise point of the reflected wave.

DETAILED DESCRIPTION OF INVENTION

Hereinafter, embodiments of the present invention will be described with reference to the drawings. In the following description, identical components or structural elements are given the same symbol. The names and functions thereof are also the same. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Tr, one of the indices for determining the degree of arteriosclerosis, is expressed as a time interval between the time of appearance of the ejection wave and the time of appearance of the reflected wave that comes back after the traveling wave is reflected from the branch in the iliac artery. For example, as described in Reference Document London G. M. et al, *Hypertension*. 1992 July; 20(1):10-19, it is known that there is a correlation between PWV calculated from the pulse propagation time between two points measured with a PWV measurement device, and Tr estimated from the pulse waveform of the artery.

Embodiment 1

Figure 1:
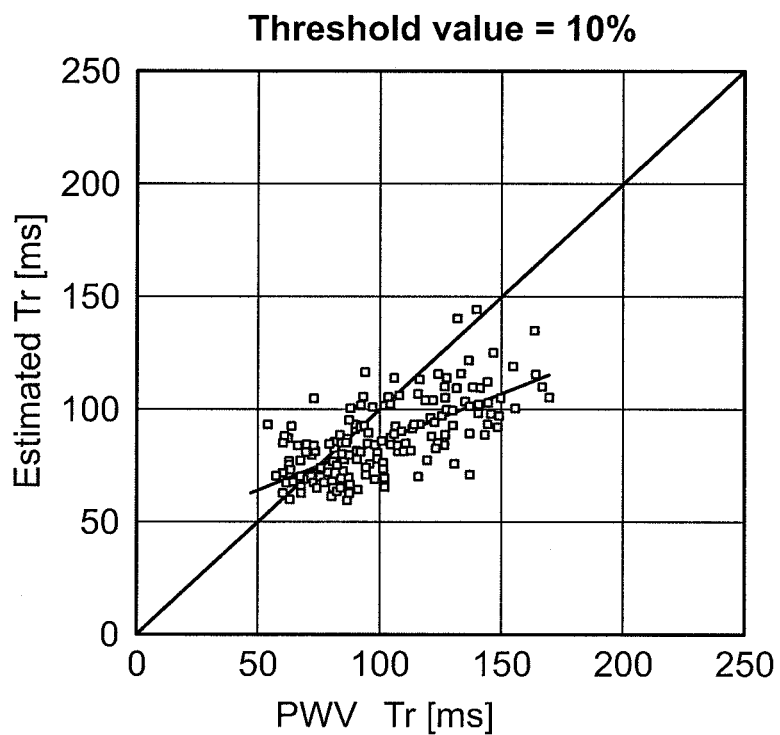
FIG. 1 shows the relationship between PWV Tr calculated from the time of pulse wave propagation at two points measured by a PWV detection device according to prior art, and Tr estimated from a pulse wave measured by detecting the time at which the threshold value is reached by the rise point of the reflected wave, with an amplitude of 10% of the reflected wave set as the threshold value, in the same subject as FIG. 17.
Figure 2:
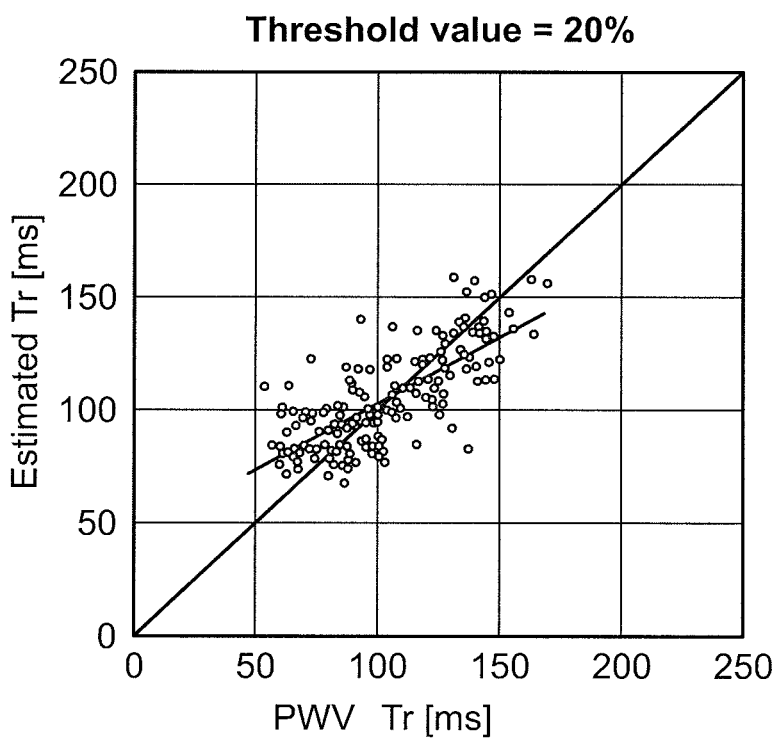
FIG. 2 shows the relationship between PWV Tr calculated from the time of pulse wave propagation at two points measured by a PWV detection device according to prior art, and Tr estimated from a pulse wave measured by detecting the time at which the threshold value is reached by the rise point of the reflected wave, with an amplitude of 20% of the reflected wave set as the threshold value, in the same subject as FIG. 17.
Figure 3:
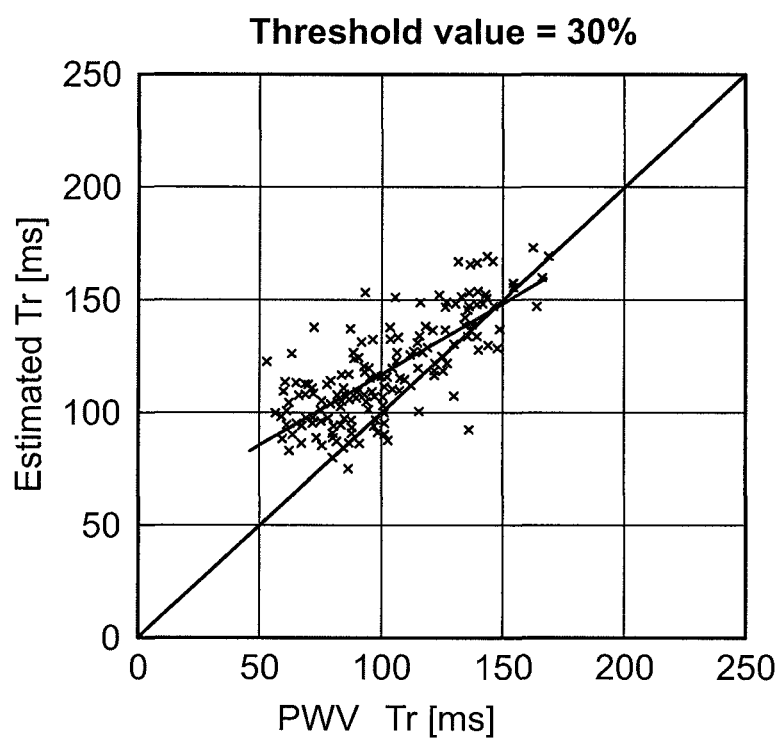
FIG. 3 shows the relationship between PWV Tr calculated from the time of pulse wave propagation at two points measured by a PWV detection device according to prior art, and Tr estimated from a pulse wave measured by detecting the time at which the threshold value is reached by the rise point of the reflected wave, with an amplitude of 30% of the reflected wave set as the threshold value, in the same subject as FIG. 17.
Figure 17:
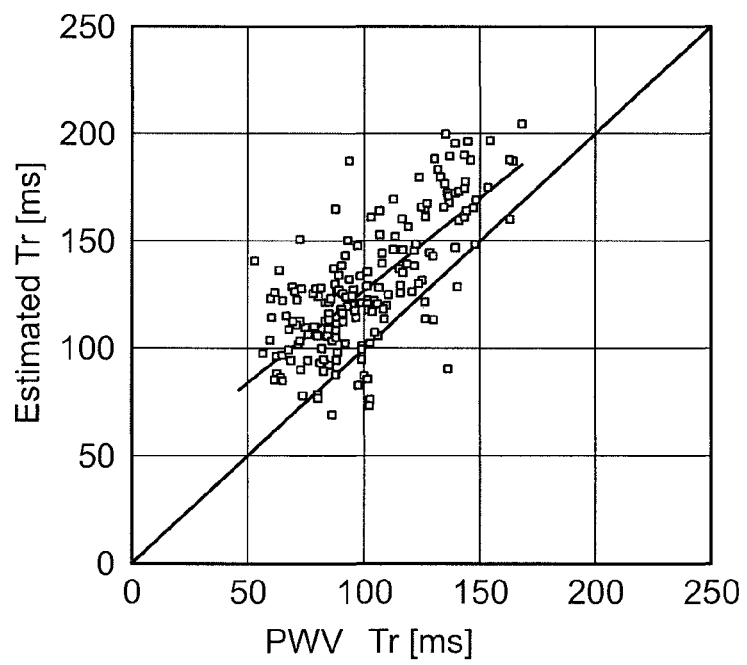
FIG. 17 is a drawing showing the correlation of Tr derived from a pulse wave measured using prior art and a PWV Tr calculated from the pulse wave propagation time between two points measured by a PWV measurement device according to prior art.
Figure 18:
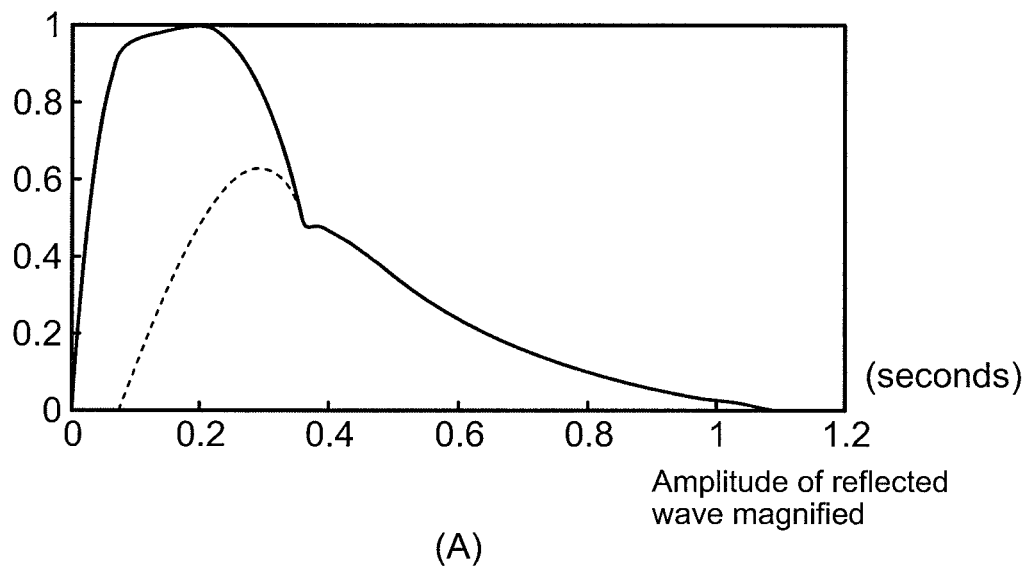
FIG. 18 is a drawing explaining the method of estimating Tr using a threshold value set from the blood pressure waveform using prior art.
Figure 18:
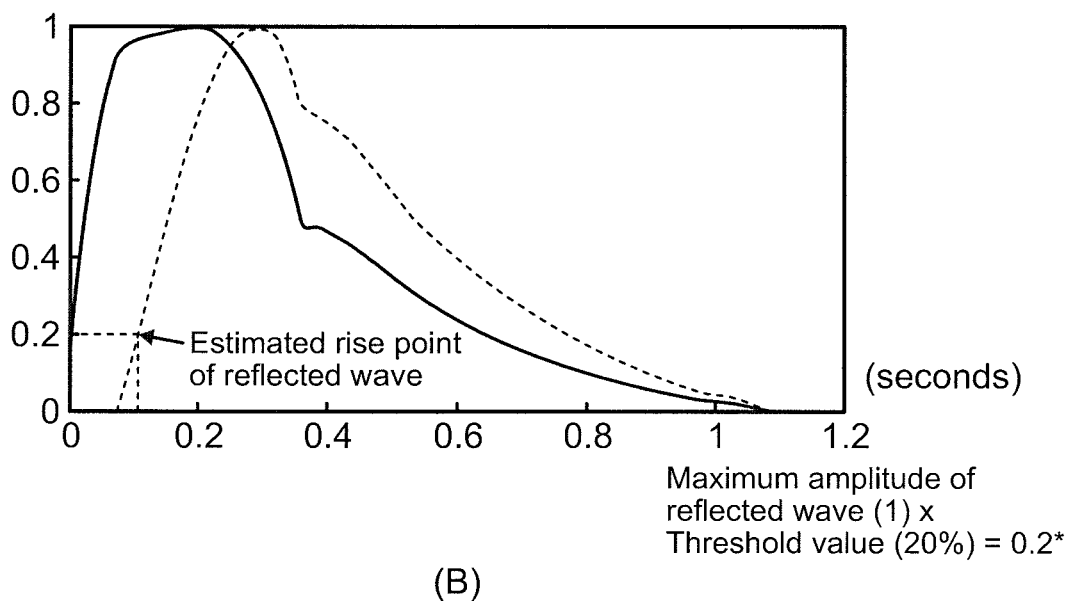

FIG. 1, FIG. 2, and FIG. 3, respectively, show the relationships between Tr calculated from the time of pulse wave propagation at two points measured by a PWV detection device according to prior art (hereinafter "PWV Tr"), Tr obtained by estimation using threshold value(s) from a ejection wave and reflected wave separated using a blood pressure waveform measured at the carotid artery, and a triangular shaped blood flow waveform (hereinafter an "estimated Tr"), in the same subject as FIG. 17.

Looking at FIG. 1, when the threshold value is set at 10% of the amplitude of the reflected wave, the difference between PWV Tr and estimated Tr is small in a subject with a short Tr, but the difference between PWV Tr and estimated Tr is large in a subject with a long Tr. Looking at FIG. 3, when the threshold value is set at 30% of the amplitude of the reflected wave, the difference between PWV Tr and estimated Tr is small in a subject with a long Tr, but the difference between PWV Tr and estimated Tr is large in a subject with a short Tr, the opposite of the case where the threshold value is 10%. FIG. 2 shows an intermediate result, when the threshold value is 20% of the amplitude of the reflected wave.

Figure 4:
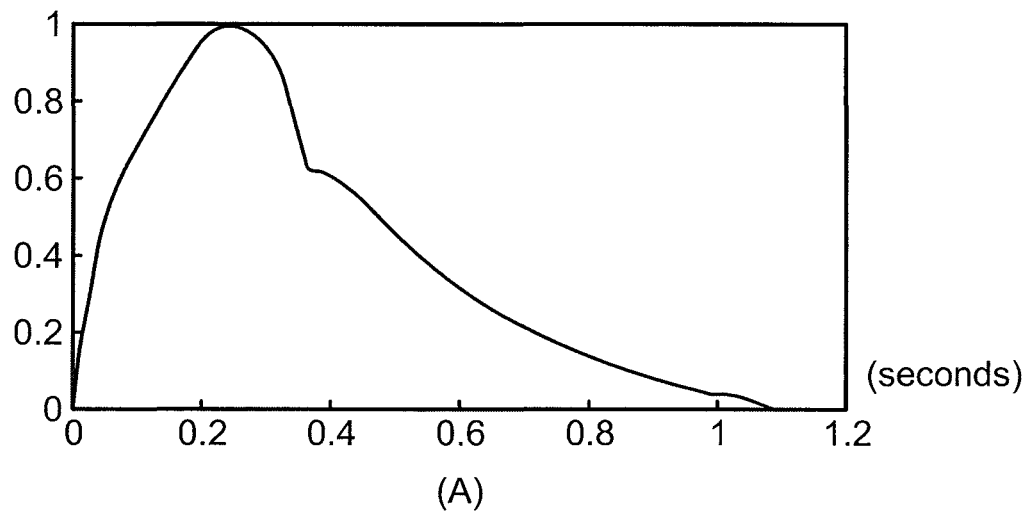
FIGS. 4 (A) and (B) show specific examples of blood pressure waveforms measured at the carotid artery in a subject with short Tr (FIG. 4 (A)) and a subject with long Tr (FIG. 4 (B)).
Figure 4:
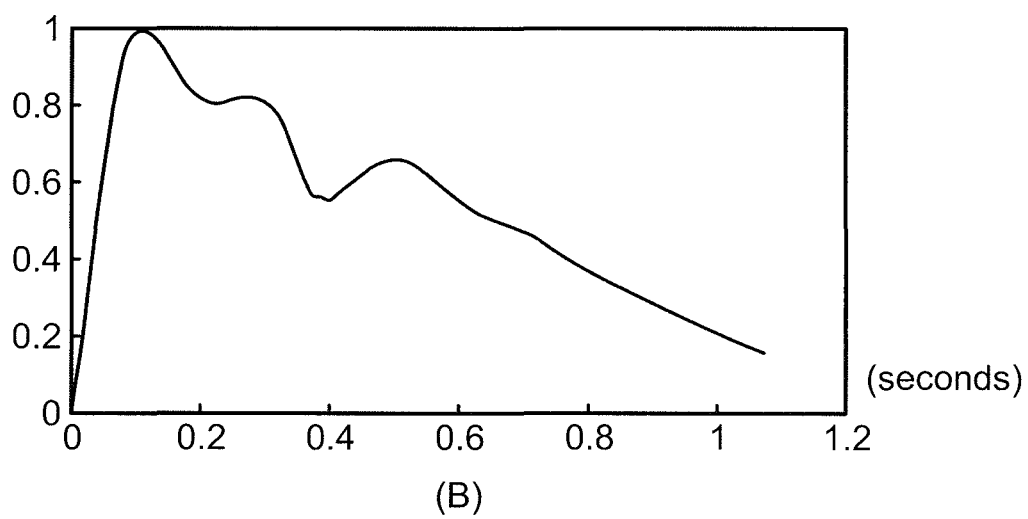
Figure 5:
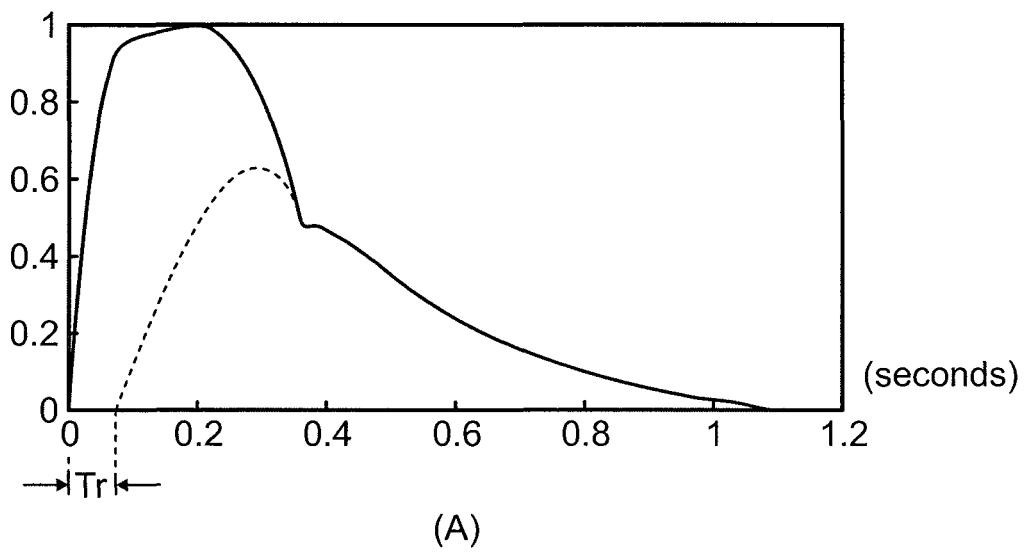
FIGS. 5 (A) and (B) are drawings showing the separation of an ejection wave (solid line) and a reflected wave (dotted line) in the blood pressure waveforms in FIGS. 4(A) and (B), respectively.
Figure 5:
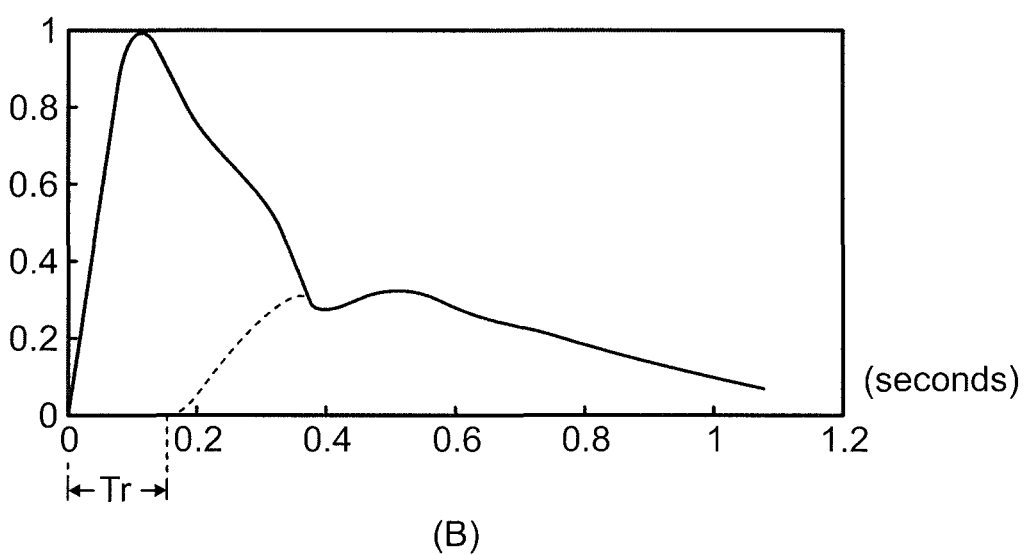
Figure 6:
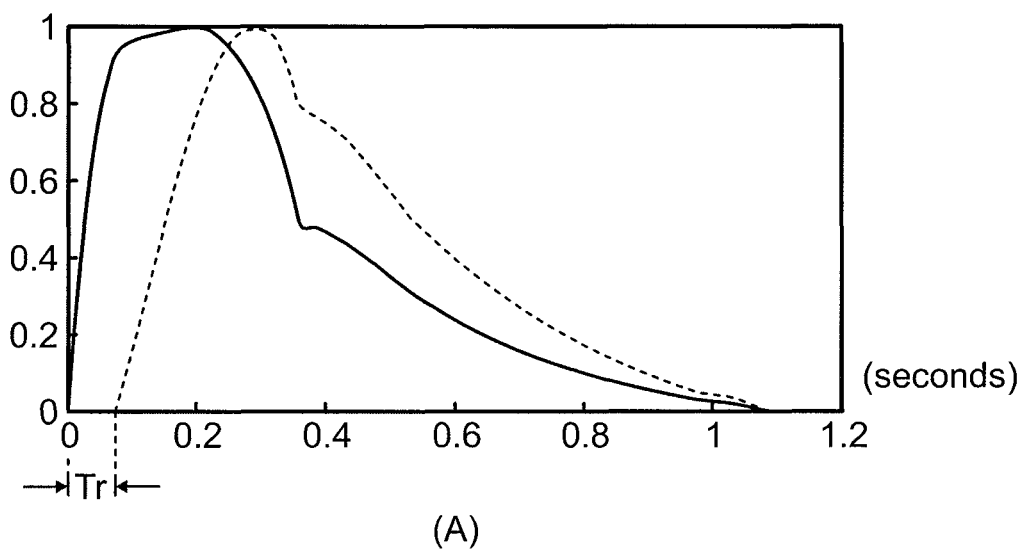
FIGS. 6 (A) and (B) are drawings showing waveforms of the reflected waves in FIGS. 5(A) and (B), respectively, with the amplitude direction enlarged until the maximum amplitude thereof is the same as the maximum amplitude of the ejection wave.
Figure 6:
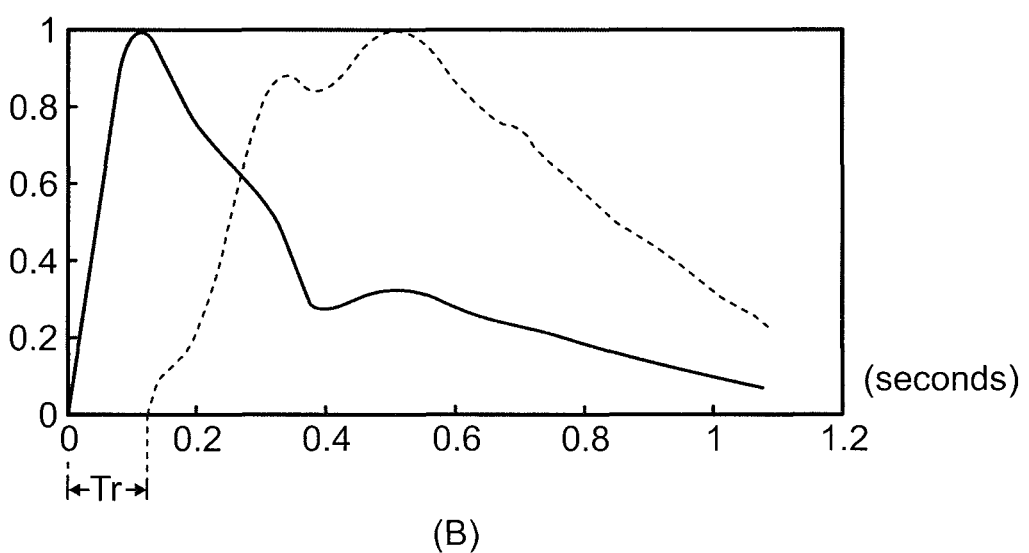

FIGS. 4(A) and (B), respectively, show specific examples of blood pressure waveforms measured at the carotid artery in a subject with a short Tr and a subject with a long Tr. FIG. 4 shows the ratio of amplitude to maximum amplitude over time, with the maximum amplitudes of the respective pulse waves assigned a value of 1. FIGS. 5(A) and (B) show the separation of the ejection wave (solid line) and reflected wave (dotted line) of the blood pressure waveforms in FIGS. 4(A) and (B) respectively using the cross correlation method. Also, FIGS. 6(A) and (B) show the waveforms of the reflected waves in FIGS. 5(A) and (B), respectively, with the maximum amplitude thereof enlarged in the amplitude direction until it is the same as the maximum amplitude of the ejection wave.

Looking at FIGS. 5(A) and (B), it can be seen that the ratio of the amplitude of the reflected wave to the amplitude of the ejection wave is greater in a subject with a short Tr. Also, the slope of the separated reflected wave from time of appearance to peak has a steeper slope at time of appearance and becomes more gradual as it approaches the peak in a subject with a short Tr (FIG. 6(A)), in comparison with a subject with a long Tr (FIG. 6(B)) who has a steep slope after appearance but then a slope that is gradual up to about 20%, and then becomes steep again thereafter. For this reason, if we consider the point where the slope of the reflected wave is steepest to be the rise point of the reflected wave, then it is appropriate to say that in a person with a short Tr, a point near the time of appearance of the reflected wave is estimated to be the rise point, and in a person with a long Tr, a point slightly after the time of appearance of the reflected wave is estimated to be the rise point.

As stated above, Tr is an index of the degree of arteriosclerosis, and the shorter the Tr, the more arteriosclerosis has progressed, and the longer the Tr the less arteriosclerosis has progressed. On the other hand, when Tr is short or in other words the reflected wave appears earlier in the blood pressure waveform, the size of the reflected wave in the blood pressure waveform is greater. And when Tr is long or in other words the appearance of the reflected wave in the blood pressure waveform is slower, the size of the reflected wave in the blood pressure waveform is smaller.

From the facts stated above, the Inventors etc. of the present invention arrived at the concept that it is possible to more accurately estimate the rise point of the reflected wave with respect to subjects with a variety of degrees of hardening of the arteries, by using a threshold value to determine the rise point of the reflected wave that follows the degree of hardening of the arteries in the subject. The degree of hardening of the arteries of the aforementioned subjects can be represented by using, for example, the size of the reflected wave appearing in the blood pressure wave, and accordingly, different threshold values can be used as the threshold value depending on the size of the reflected wave for the purpose of determining the rise point of the reflected wave.

The aforementioned degree of arteriosclerosis can be represented by using the ratio of the amplitude of the ejection wave and the amplitude of the reflected wave (the AI (augmentation index) value) obtained from the blood pressure wave. In terms of values representing the aforementioned size of the reflected wave appearing in the blood pressure wave, the values $\alpha$ obtained from Equations (1)-(3) below according to an AI value calculated from a measured blood pressure waveform are used as the threshold value $\alpha$ for the purpose of determining the rise point. Note also that in Equation (2) below, coefficient a and coefficient b are experimental values determined from the relationship between previously measured AI value and rise point of the reflected wave in a large number of subjects, such that as the AI value decreases, $\alpha$ approaches $\alpha 2$, and as the AI value increases $\alpha$, approaches $\alpha 1$.

$$\alpha = \alpha 2 (AI < AI\_2) \quad \text{Equation (1)}$$

$$\alpha = AI \times a + b (AI\_2 \leq AI \leq AI\_1) \quad \text{Equation (2)}$$

$$\alpha = \alpha 1 (AI\_1 < AI) \quad \text{Equation (3)}$$

Figure 7:
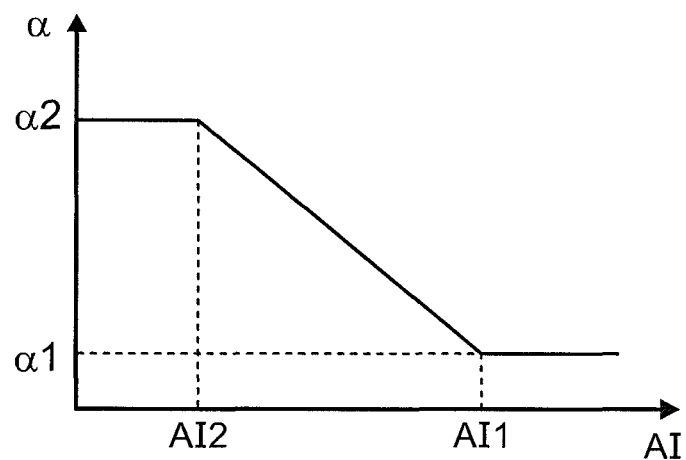
FIG. 7 is a drawing showing the relationship between the AI value and threshold value α, expressed as an equation of correlation between the AI value and threshold value α.

FIG. 7 shows the relation between AI and the threshold values $\alpha$ obtained from Equations (1)-(3). As shown in FIG. 7, value $\alpha 1$ is used as threshold value $\alpha$ when the calculated AI value is greater than first threshold value AI1, and value $\alpha 2$, greater than value $\alpha 1$, is used as threshold value $\alpha$ when the AI value is less than AI2, a second threshold value smaller than AI1, and further, when the AI value is between AI2 and AI1, threshold value $\alpha$ approaches $\alpha 2$ as the AI value decreases, and approaches $\alpha 1$ as the AI value increases. As a result, when the AI value is greater (the amplitude of the reflected wave is greater), threshold value $\alpha$ is set lower, and conversely when the AI value is smaller (the amplitude of the reflected wave is smaller), threshold value $\alpha$ is set higher. Thus, more accurate Tr values can be calculated by using a variable setting of threshold values according to the AI value of the blood pressure waveform measured from the subject.

Figure 8:
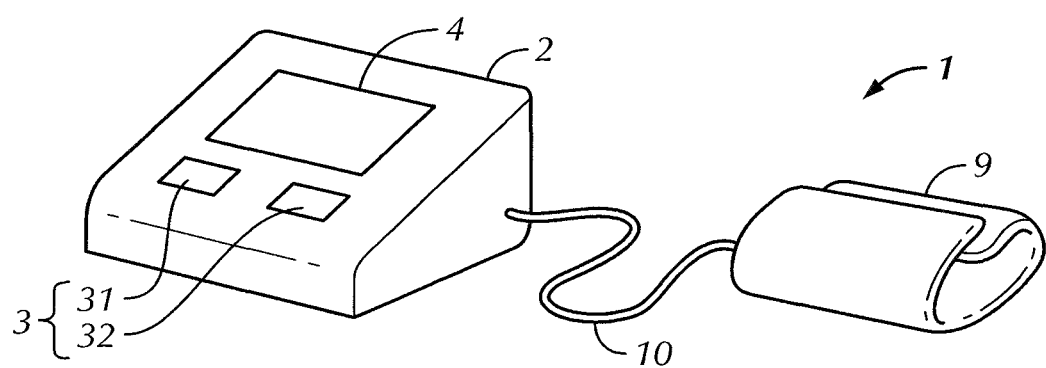
FIG. 8 is a drawing showing a specific example of the external appearance of a blood pressure data measurement device (hereinafter abbreviated "measurement device") according to one or more embodiments of the present invention.

FIG. 8 shows a specific example of the external appearance of a blood pressure data measurement device (hereinafter abbreviated "measurement device") according to one or more embodiments of the present invention.

In FIG. 8, measurement device 1 includes base unit 2 connected by air tube 10, and arm cuff 9 mounted on the upper arm. On the front panel of base unit 2 are placed display unit 4 displaying a variety of data including results of measurement, and operating unit 3 operated for the purpose of giving various instructions to measurement device 1. Operating unit 3 includes switch 31 operated to turn the power supply on and off, and switch 32 operated to give instructions to start measurement.

Figure 9:
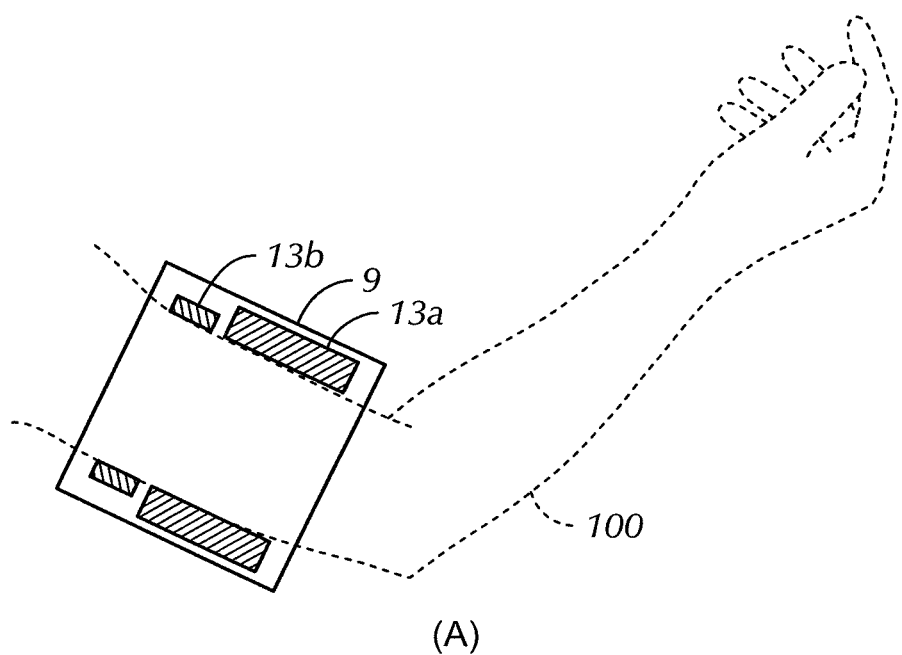
FIGS. 9 (A) and (B) are drawings showing a specific example of the structure of the measurement position and armband.
Figure 9:
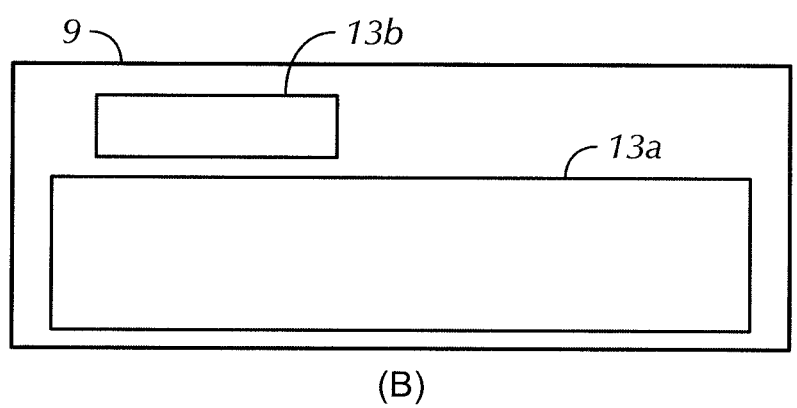

In FIG. 9(A) and FIG. 9(B), arm band 9 is provided with an air bladder in the form of a fluid pouch for the purpose of compressing the body. Said air bladder includes an air bladder 13A, a fluid pouch used for the purpose of measuring blood pressure data in the form of blood pressure, and an air bladder 13B, a fluid pouch used for the purpose of measuring blood pressure data in the form of a pulse wave. The size of air bladder 13B is for example approximately 20 mm×200 mm. Also, according to one or more embodiments of the present invention, the air capacity of air bladder 13B is not more than ⅕ the air capacity of air bladder 13A.

In measuring a pulse wave using measurement device 1, arm band 9 is wrapped around the measurement location, upper arm 100, as shown in FIG. 9(A). In this state, blood pressure data is measured by pressing switch 32, and an index for the purpose of determining the degree of arteriosclerosis is calculated on the basis of the blood pressure data. Here, "blood pressure data" refers to data related to blood pressure obtained by measurement from the body, and specifically refers to blood pressure values, blood pressure waveforms (pulse wave shapes), pulse rate, etc.

Figure 10:
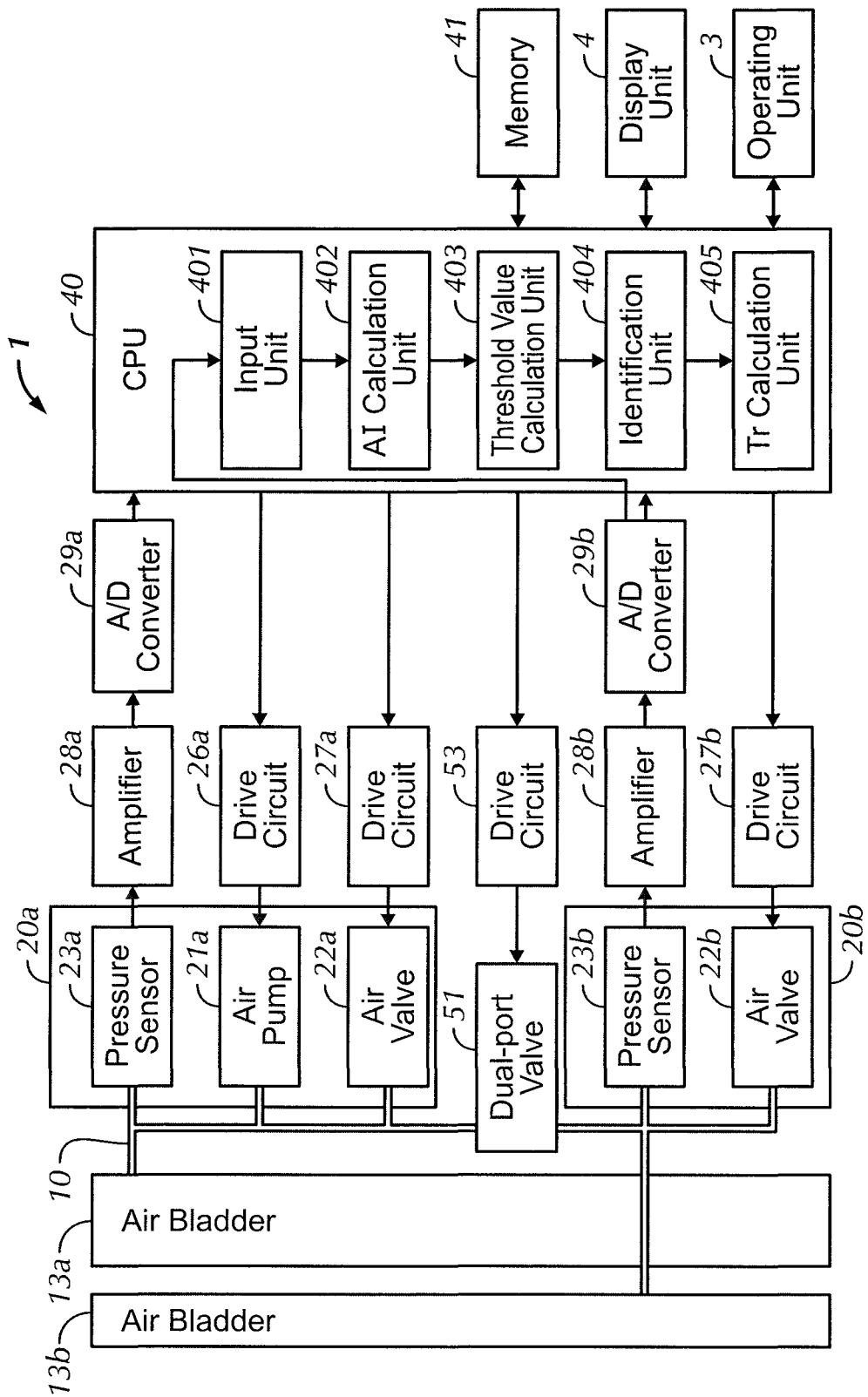
FIG. 10 is a block diagram showing a specific example of the structure of the measurement device.

FIG. 10 is a block diagram showing a specific example of the structure of the measurement device.

In FIG. 10, measurement device 1 includes air system 20A connecting through air tube 10 to air bladder 13A, and air system 20B connecting through air tube 10 to air bladder 13B, and CPU (central processing unit) 40. Air system 20A includes air pump 21A, air valve 22A, and pressure sensor 23A. Air system 20B includes air valve 22B and pressure sensor 23B.

Air pump 21A is connected to drive circuit 26A, and drive circuit 26A is further connected to CPU 40. Air pump 21A is driven by drive circuit 26A according to instructions received from CPU 40, and applies pressure to air bladder 13A by sending compressed air to air bladder 13A.

Air valve 22A is connected to drive circuit 27A, and drive circuit 27A is further connected to CPU 40. Air valve 22B is connected to drive circuit 27B, and drive circuit 27B is further connected to CPU 40. The open/closed state of air valves 22A, 22B is controlled, respectively, by drive circuits 27A, 27B according to instructions received from CPU 40. By controlling the open/closed state thereof, air valves 22A, 22B, respectively, maintain or decrease pressure within air bladders 13A, 13B. Pressure inside air bladders 13A, 13B is controlled by this means.

Pressure sensor 23A is connected to amplifier 28A, and amplifier 28A is connected to A/D converter 29A, and further A/D converter 29A is connected to CPU 40. Pressure sensor 23B is connected to amplifier 28B, and amplifier 28B is connected to A/D converter 29B, and further A/D converter 29B is connected to CPU 40. Pressure sensors 23A, 23B, respectively, detect pressure in air bladders 13A, 13B, and output signals to amplifiers 28A, 28B according to the values detected. The output signals are amplified by amplifiers 28A, 28B, and digitalized by A/D converters 29A, 29B, then input to CPU 40.

The air tube from air bladder 13A and the air tube from air bladder 13B are connected by dual-port valve 51. Dual-port valve 51 is connected to drive circuit 53, and drive circuit 53 is further connected to CPU 40. Dual-port valve 51 has a valve for the side of air bladder 13A and a valve for the side of air bladder 13B, and opens and closes said valves by being driven by drive circuit 53, which receives instructions from CPU 40.

Memory 41 stores programs executed by CPU 40. CPU 40 reads and executes programs from memory 41 on the basis of instructions input to operating unit 3 placed in base unit 2 of the measurement device, and outputs control signals by execution of said programs. Also, CPU 40 outputs measurement results to, for example, display unit 4 and memory 41. Memory 41 stores measurement results and also stores data related to subjects as necessary, including at least age. In addition, CPU 40 is used for reading of data and computation related to said measured persons, as necessary according to the execution of programs.

Further in FIG. 10, CPU 40 contains functions for the purpose of calculating Tr (estimated Tr) as an indicator for determining the degree of arteriosclerosis according to the aforementioned principle, namely, input unit 401 for the purpose of obtaining a blood pressure waveform by receiving input of pressure signals from pressure sensor 23B, AI calculation unit 402 for the purpose of calculating AI values from blood pressure waveforms, threshold value calculation unit 403 for the purpose of calculating threshold values α for detection of a rise point in the reflected wave from the detected AI values by using aforementioned Equations (1)-(3), identification unit 404 for the purpose of identifying the rise point in the reflected wave and the rise point in the ejection wave of the blood pressure wave form, and Tr calculation unit 405 for the purpose of calculating Tr (estimated Tr) as an indicator for the purpose of determining the degree of arteriosclerosis from the delay in time of the appearance of the rise point in the ejection wave and the rise point in the reflected wave of the blood pressure waveform. These are primarily functions formed in CPU 40 as CPU 40 reads and executes programs stored in memory 41 according to control signals from operating unit 3, however, at least some part of these functions may also be formed by hardware configuration.

Identification unit 404 obtains a one beat portion of the blood pressure waveform from the blood pressure waveform input, then identifies the rise point thereof, in other words the starting point of the blood pressure waveform, from the rise point of the ejection wave. Also, identification unit 404 identifies the rise point of the reflected wave in the blood pressure waveform using the aforementioned threshold value α.

Figure 11:
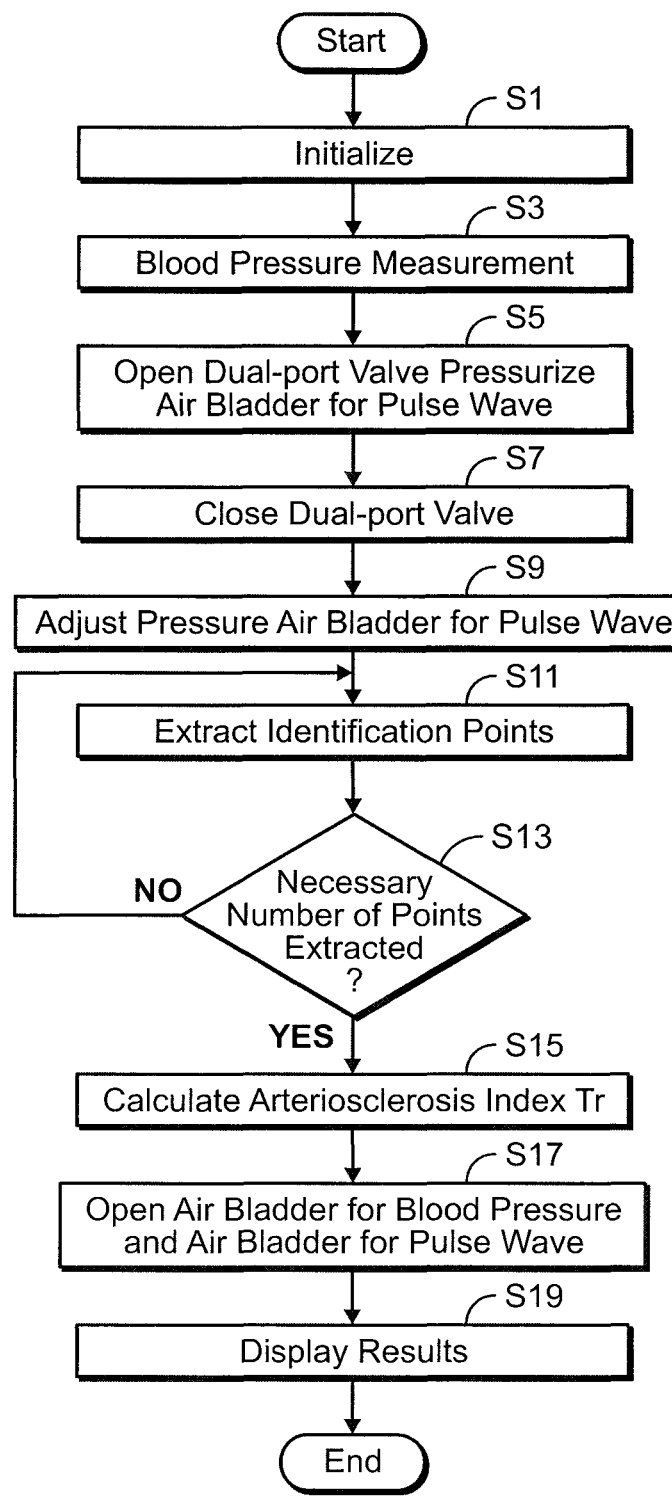
FIG. 11 is a flowchart showing the operation of the measurement device.
Figure 13:
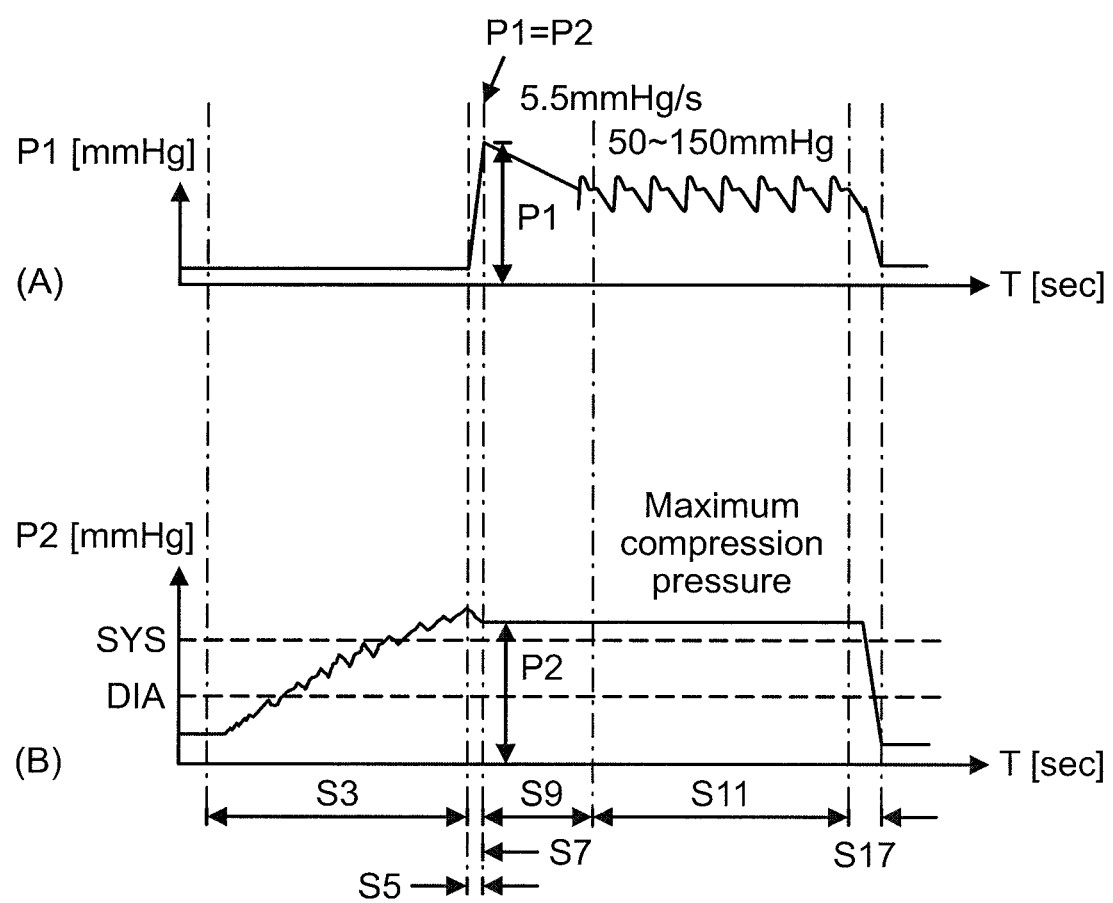
FIG. 13 is a descriptive drawing of changes in pressure inside a compression air bladder and an air bladder for measurement during operation of the measurement device.

FIG. 11 is a flowchart showing the operation of the measurement device. The operation shown in FIG. 11 starts when the measuring person depresses switch 32. This operation causes CPU 40 to read programs stored in memory 41 and to control the various units shown in FIG. 10. Also, pressure changes in air bladders 13A, 13B during operation by measurement device 1 are described with reference to FIG. 13. FIG. 13(A) shows changes over time in pressure P1 in air bladder 13B, and FIG. 13(B) shows changes over time in pressure P2 in air bladder 13A. S3 through S17 placed on the time axes of FIGS. 13(A) and (B) correspond to each of the operations in the measurement operation of measurement device 1, described below.

In FIG. 11, when operation starts, each unit in CPU 40 is initialized in Step S1. In Step S3, CPU 40 outputs a control signal to air system 20A to start applying pressure in air bladder 13A, and measures blood pressure in the process of applying pressure. Measurement of blood pressure in Step S3 is performed by measurement according to the oscillometric method performed in a normal blood pressure monitor.

When blood pressure measurement in Step S3 is completed, in Step S5 CPU 40 sends a control signal to drive circuit 53 to start both the valve on the side of air bladder 13A and the valve on the side of air bladder 13B of dual-port valve 51. By this means, air bladder 13A and air bladder 13B operate together, and a part of the air in air bladder 13A moves into air bladder 13B, increasing pressure in air bladder 13B.

In the example in FIG. 13(B), from the start of application of pressure in Step S3 to the completion of measurement, pressure P2 in air bladder 13A increases up to a pressure higher than the maximum blood pressure value. Then in Step S5, by opening said valves in dual-port valve 51 a portion of the air in air bladder 13A moves into air bladder 13B, reducing pressure P2. At the same time, as shown in FIG. 13(A), pressure P1 in air bladder 13B increases rapidly. Then at the point when pressure P1 and pressure P2 are equal, in other words the point when the internal pressures in air bladders 13A, 13B are equal, movement of air from air bladder 13A into air bladder 13B ends. In Step S7, CPU 40 outputs a control signal at this time to drive circuit 53, closing both valves in dual-port valve 51 that were opened in Step S5. FIGS. 13(A) and (B) show that pressure P1 and pressure P2 are equal at the point of Step S7. Because the capacity of air bladder 13B is smaller than the capacity of Air bladder 13A as shown in FIG. 2(A), the reduction in pressure P2 in step S5 is not great, and thus, at the time of Step S7, both pressure P1 and Pressure P2 are higher than the maximum blood pressure value.

Then, in Step S9, CPU 40 outputs a control signal to drive circuit 27B, adjusting pressure P1 in air bladder 13B downward until it reaches a pressure appropriate for measurement of the pulse wave. According to one or more embodiments of the present invention, the degree of this downward pressure adjustment should be, for example, approximately 5.5 mmHg/sec. Also, according to one or more embodiments of the present invention, a pressure of 50-150 mmHg is used for measuring a pulse wave. Because both valves of dual-port valve 51 are closed at this time, the extremity side of the measurement location is under application of pressure P2 in air bladder 13A, a pressure higher than the maximum blood pressure, and thus is in an avascularized state.

With the extremity side in an avascularized state, in Step S11 CPU 40 performs operations to extract characteristic points from the blood pressure waveform each time a one beat portion of the blood pressure waveform is input via the pressure signal from pressure sensor 23B.

Figure 12:
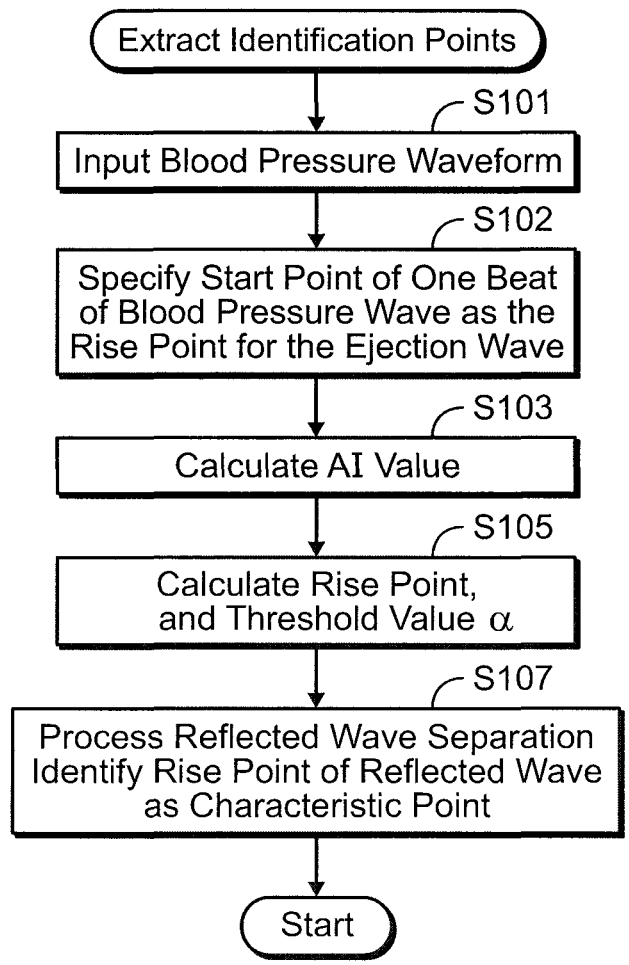
FIG. 12 is a flowchart showing the operation for the purpose of extracting characteristic points in step S11 of FIG. 11.

FIG. 12 is a flowchart showing the operation for the purpose of extracting characteristic points in step S11 of FIG. 11. Looking at FIG. 12, in Step S101, CPU 40 receives the pressure signal from pressure sensor 23B and identifies a one beat portion of the blood pressure waveform. Then in Step S102, CPU 40 identifies the start point of the blood pressure waveform as the rise point in the ejection wave.

In Step S103, CPU 40 identifies the maximum amplitude of the ejection wave and the maximum amplitude of the reflected wave in the blood pressure waveform, and by calculating the ratio thereof obtains the AI value.

CPU 40 has previously stored the aforementioned Equations (1)-(3) in order to calculate threshold value α, used for the purpose of identifying the rise point of the reflected wave from the Maximum amplitude of a one beat portion of blood pressure waveform, by using the AI value obtained from that blood pressure waveform. Then in Step S105, threshold value α is calculated by substituting the AI value calculated in Step S103 into said equations.

From the blood pressure waveform identified in Step S101, CPU 40 in Step 107 identifies the rise point of the reflected wave, as the time at which an amplitude obtained by multiplying the maximum amplitude of the reflected wave by threshold value α is reached, and stores that point as a characteristic point.

The measurement operations in Step S11 are performed by repetition of input of a predetermined number of blood pressure waveforms (for example, 10 beats). During this interval, pressure P1 in air bladder 13B is maintained at a pressure appropriate for measurement of a pulse wave as shown in FIG. 13(A), and pressure P2 in air bladder 13A is maintained at a pressure higher than the maximum blood pressure value as shown in FIG. 13(B). By this means, the state of avascularization in the peripheral side of the measurement position is maintained.

Once the input of the aforementioned blood pressure wave is repeated a predetermined number of times (for example, 10 beats), (thus YES in Step 13), then in Step S15 CPU 40 calculates Tr (estimated Tr) as an indicator of the degree of arteriosclerosis, by using the average value of the values from said repeated input and the identified rise point of the ejection wave. Then in Step S17, CPU 40 outputs control signals to drive circuits 27A, 27B to open air valves 22A, 22B thus releasing air bladders 13A, 13B to atmospheric pressure. In the example in FIGS. 13(A) and (B), pressure P1 and P2 rapidly drop to atmospheric pressure in the interval of Step S17.

The measurement results, such as the calculated maximum blood pressure value (SYS), minimum blood pressure value (DIA), indicators of the degree of arteriosclerosis, and measured pulse wave etc. undergo processing for the purpose of display on display unit 4 placed in base unit 2, and are displayed.

Figure 14:
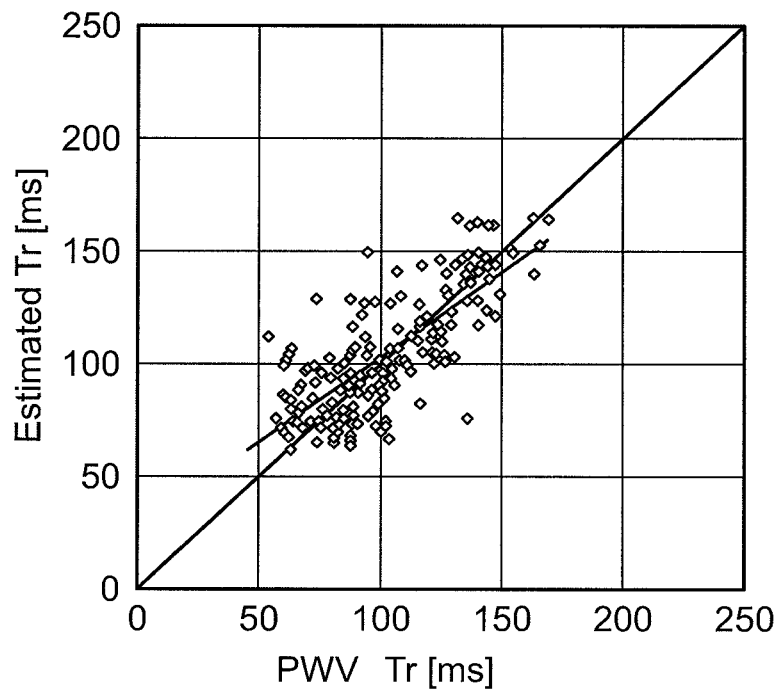
FIG. 14 is a drawing showing the relationship between PWV Tr calculated from the pulse wave propagation time at two points measured by a PWV measuring device and Tr calculated by the measurement device.

FIG. 14 shows the relationship between PWV Tr calculated from the pulse wave propagation time at two points measured by a PWV measuring device and Tr calculated by measurement device 1. As shown in FIG. 14, the estimated Tr calculated by measurement device 1 is closer to the PWV Tr than the estimated Tr calculated by methods according to prior art (FIG. 17). Specifically, it can be seen that the difference between PWV Tr and the estimated Tr calculated by measurement device 1 is less than that shown in FIG. 17. Because the PWV Tr calculated on the basis of measurement of wave propagation speed at two points is the most accurate Tr value feasible at the present time, measurement device 1 according to one or more embodiments of the present invention is capable of a smaller margin of error in calculated Tr (estimated Tr) than prior methods of calculating pulse wave Tr, and thus, it clearly is capable of accurately determining the degree of arteriosclerosis.

Embodiment 2

Whereas the first embodiments uses an AI value as a value expressing the size of the reflected wave appearing in the blood pressure waveform, which reflects the degree of hardening of the arteries of the subject, it is also possible to make an estimation using values calculated by differentiation of the blood pressure waveform (hereinafter abbreviated "provisional TR value") instead of the AI value.

Provisional Tr values calculated by differentiation from the blood pressure waveform and capable of use in detecting the rise point of the reflected wave include, for example, a point corresponding to the maximum of a second-order differential curve of the blood pressure waveform, and a point corresponding to the falling zero-crossing point of a fourth-order differential curve of the blood pressure waveform.

When a value calculated by differentiation of the blood pressure waveform is used as a provisional Tr value, CPU 40 of measurement device 1 stores equations (1')-(3') in place of the aforementioned equations (1)-(3).

$$\alpha = \alpha 1 \text{(differential } Tr < Tr\_2)\quad \text{Equation (1')},$$

$$\alpha = \text{Provisional } Tr \times a' + b' (Tr\_2 \leq \text{differential } Tr \leq Tr\_1)\quad \text{Equation (2')},$$

$$\alpha = \alpha 2 (Tr\_1 < \text{differential } Tr)\quad \text{Equation (3')}.$$

Figure 15:
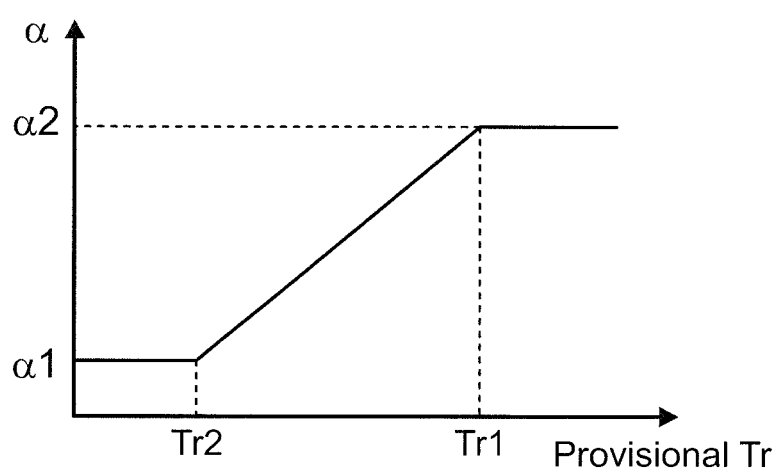
FIG. 15 is a drawing expressing the relationship between provisional Tr value and threshold value α.
Figure 16:
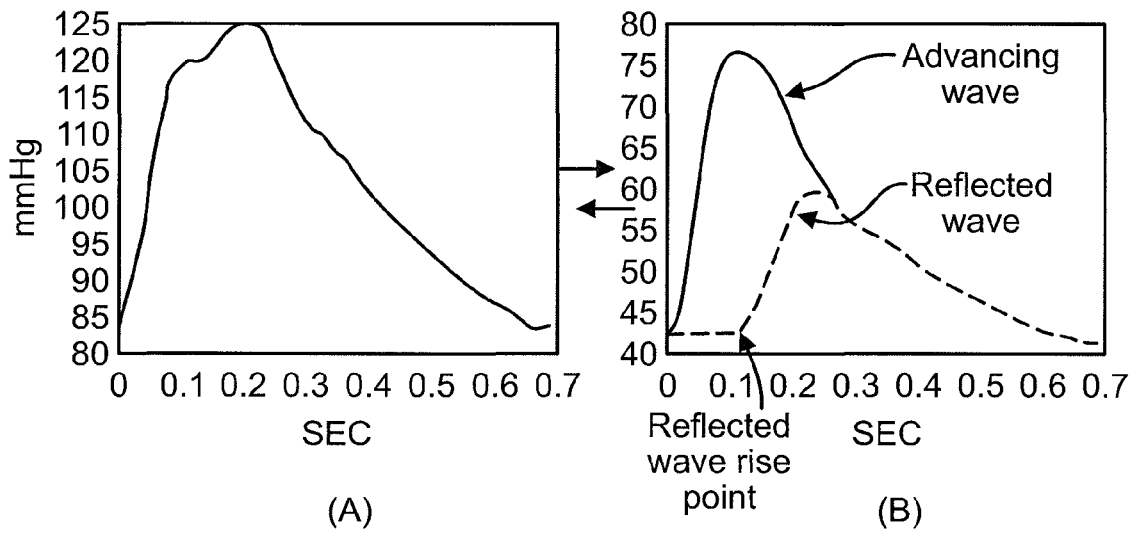
FIG. 16 is a drawing for the purpose of explaining the method of separating the ejection wave and reflected wave using the blood pressure wave of the aorta and an estimated value of the blood flow volume waveform, disclosed in Patent Publication 2009-517140.

FIG. 15 is a drawing expressing the relationship between provisional Tr value and the threshold value α obtained from Equations (1')-(3'). As shown in FIG. 15, using value α2 as threshold value α when the provisional Tr value is greater than first threshold value Tr1, using value α1 less than value α2 as threshold value α when provisional Tr value is less than Tr2, a second threshold value less than Tr1, and when provisional Tr value is between Tr2 and Tr1, using a value that approaches α1 as the provisional Tr value decreases, and approaches α2 when the provisional Tr value increases, as threshold value α. Thus, conversely to the case of the value of AI according to the first embodiment, threshold value α is set high when provisional Tr is high, and threshold value α is set low when provisional Tr is low. The estimated Tr value is calculated by using a variable threshold value that is set in this manner according to the provisional Tr value. The configuration of the second embodiment is otherwise fundamentally the same as that of the first embodiment.

Embodiments of the present invention are not limited to the previously described embodiments, and may for example use the age of the subject as the degree of hardening of the arteries of the subject, based on the fact that in general, arteriosclerosis is more advanced at higher ages and less advanced at younger ages. When subject age is used as the degree of hardening of the arteries of the subject, the AI value decreases in correlation to increases in subject age, and therefore CPU 40 in measurement device 1 stores equations like those in the aforementioned Equations (1)-(3) using subject age as the parameter.

The relation between subject age and threshold value α obtained from equations like Equations (1)-(3), as with the relation with the AI value, is that when subject age is greater than first threshold value Ag1, value α1 is used as threshold value α, and when subject age is less than second threshold value Ag2, value α2 greater than value α1 is used as threshold value α, and when subject age is between Ag2 and Ag1, the value used for threshold a approaches α2 as the age goes lower and approaches α1 as the age goes higher.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A device for measuring blood pressure and calculating an index of degree of arteriosclerosis of a patient, the device comprising:
   a cuff for wrapping around a measurement location of a patient, the cuff containing an air bladder;
   an air pressure adjustor that adjusts an internal pressure of the air bladder;
   a pressure sensor that detects changes of the internal pressure of the air bladder; and
   a computation device that obtains a blood pressure waveform based on the changes of internal pressure of the air bladder detected by the pressure sensor, separates and identifies an ejection wave component and a reflected wave component from the blood pressure waveform, and calculates an index of degree of arteriosclerosis of the patient, the computation device further comprising:
   a threshold value setting portion that variably sets a threshold value based on an index that expresses a characteristic of the blood pressure waveform with respect to a point of appearance of the reflected wave in the blood pressure waveform; and a rise point estimating portion that estimates a rise point of the reflected wave by calculating an x-coordinate value of a point based on a maximum amplitude of the reflected wave and the threshold value, wherein the index of degree of arteriosclerosis is obtained by calculating a time difference in appearance between the ejection wave and the reflected wave based on the estimated rise point of the reflected wave.

2. The device according to claim 1, wherein the index expressing the characteristic of the blood pressure waveform is an AI (augmentation index) value of the blood pressure waveform.

3. The device according to claim 1, wherein the measurement location is an upper arm of the patient.

4. A device for measuring blood pressure and calculating an index of degree of arteriosclerosis of a patient, the device comprising:

means containing an air bladder for wrapping around a measurement location of a patient;

means for adjusting an internal pressure of the air bladder;

means for detecting changes of the internal pressure of the air bladder; and means for obtaining a blood pressure waveform based on the changes of internal pressure of the air bladder detected by the pressure sensor, separating and identifying an ejection wave component and a reflected wave component from the blood pressure waveform, and calculating an index of degree of arteriosclerosis of the patient, the means further comprising:

means for variably setting a threshold value based on an index that expresses a characteristic of the blood pressure waveform with respect to a point of appearance of the reflected wave in the blood pressure waveform; and means for estimating a rise point of the reflected wave by calculating an x-coordinate value of a point based on a maximum amplitude of the reflected wave and the threshold value, wherein the index of degree of arteriosclerosis is obtained by calculating a time difference in appearance between the ejection wave and the reflected wave based on the estimated rise point of the reflected wave.

5. The device according to claim 4, wherein the index expressing the characteristic of the blood pressure waveform is an AI (augmentation index) value of the blood pressure waveform.

6. The device according to claim 4, wherein the measurement location is an upper arm of the patient.

* * * * *